ORTHODONTIC BRACKET ASSEMBLY

[19] United States Patent
Daisley et al.

[11] 4,415,330
[45] Nov. 15, 1983

[54] ORTHODONTIC BRACKET ASSEMBLY

[75] Inventors: Richard J. Daisley, Ontario; Lawrence S. Ring, Glendora, both of Calif.

[73] Assignee: Sybron Corporation, Rochester, N.Y.

[21] Appl. No.: 343,605

[22] Filed: Aug. 31, 1981

Related U.S. Application Data

[63] Continuation of Ser. No. 36,258, May 4, 1979, abandoned.

[51] Int. Cl.³ .............................................. A61C 3/00
[52] U.S. Cl. .......................................... 433/16; 433/8
[58] Field of Search ................... 433/8, 9, 10, 11, 12, 433/13, 14, 15, 16, 17, 18

[56] References Cited

U.S. PATENT DOCUMENTS

| | | | |
|---|---|---|---|
| 2,701,913 | 2/1955 | Lane | 433/16 |
| 3,353,271 | 11/1967 | Blechman | 433/18 |
| 3,477,128 | 11/1969 | Andrews | 433/16 |
| 3,660,900 | 5/1972 | Andrews | 433/16 |
| 3,775,850 | 12/1973 | Northcutt | 433/9 |
| 3,881,252 | 5/1975 | Andrews | 433/16 |
| 3,932,940 | 1/1976 | Andren | 433/9 |
| 4,139,945 | 2/1979 | DiGiulio | 433/16 |

OTHER PUBLICATIONS

Rocky Mountain Catalog, 1-1979, p. C-4.

*Primary Examiner*—John J. Wilson
*Attorney, Agent, or Firm*—Robert A. Gerlach; Robert J. Bird

[57] ABSTRACT

An orthodontic bracket assembly is adapted for use with an arch wire in straightening a tooth having a crown long axis preferably disposed at a particular angle with respect to an occlusal plane. The bracket assembly includes a base for fixing the assembly to the tooth and at least one tie wing having a fixed relationship with the base. The tie wing has a facial surface defined by a mesial edge, a distal edge, a gingival edge and an occlusal edge. At least one of the gingival edge and the occlusal edge are disposed at the particular angle with respect to at least one of the mesial edge and the distal edge of the tie wing, so that the facial surface of the tie wing has a generally rhomboidal configuration. This facilitates alignment of the assembly with respect to the occlusal plane and the crown long axis of the tooth.

1 Claim, 9 Drawing Figures

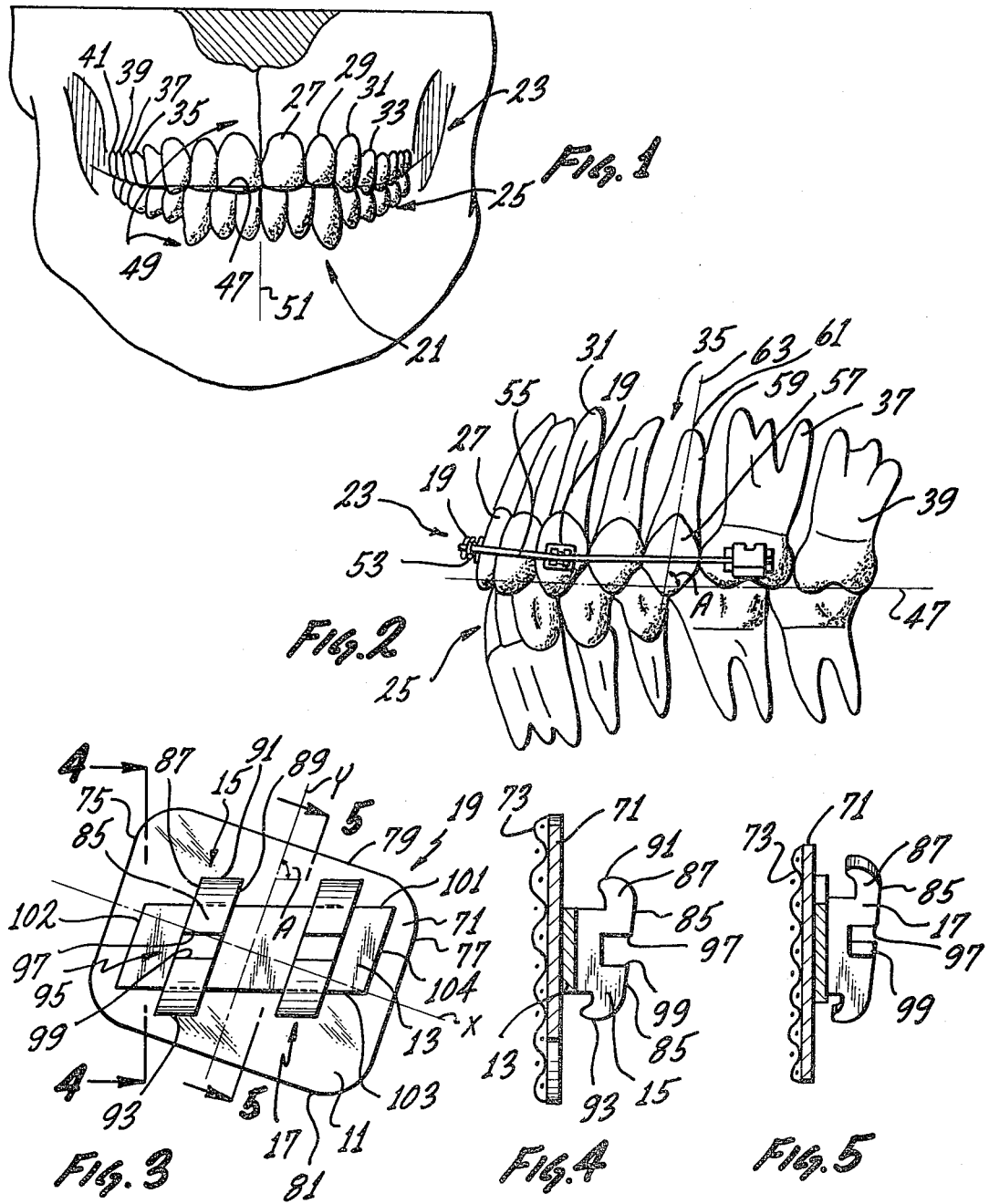

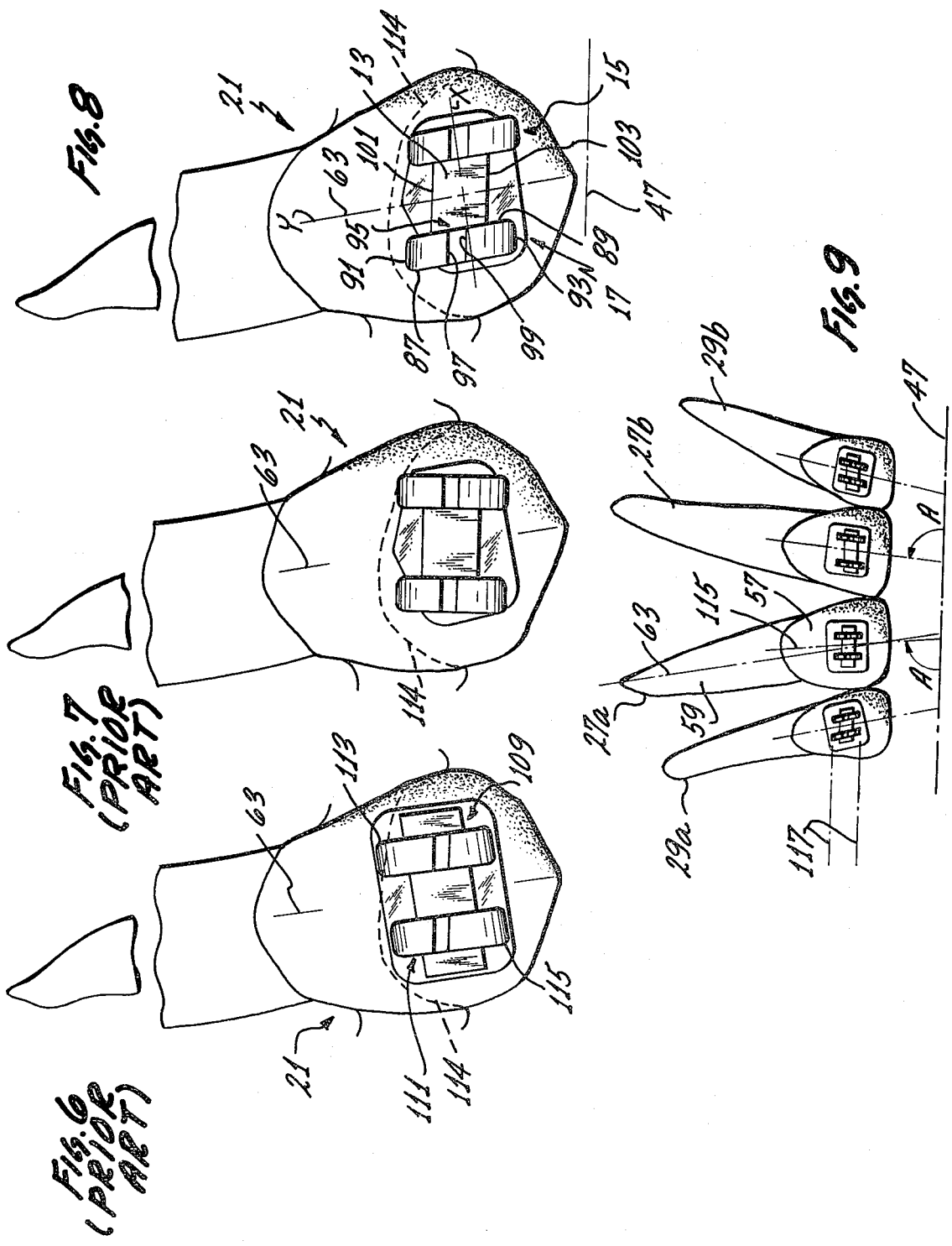

ORTHODONTIC BRACKET ASSEMBLY

This is a continuation, of application Ser. No. 036,258, filed May 4, 1979, now abandoned.

BACKGROUND OF THE INVENTION

The present invention relates generally to orthodontic bracket assemblies and more specifically to a bracket assembly particularly adapted for use in a bonding method of straightening teeth.

Prior Art Statement

Various methods are presently in use for correcting the orientation of irregular teeth. It is generally accepted that each tooth has a particular location in the arch and a preferred angle between its long axis and occlusal plane. In the mouth, the tooth long axis can best be approximated by visualizing the long axis of the crown, the only visual component of the tooth. Therefore, the preferred angle referred to above can be more practically defined as the normal angle between the crown long axis of a particular tooth and the occlusal plane.

In orthodontics, an arch wire is used to apply unidirectional and torquing forces to the irregular teeth. The arch wire is attached to the teeth by means of a bracket assembly. In the past, this assembly included a band which encircled the crown of the tooth, and a bracket including tie wings and a flange which were fixed to the band prior to mounting. These tie wings had horizontal components which were disposed generally perpendicular to its vertical components and which were aligned generally parallel to the horizntal edges of the band. It follows that these brackets of the prior art were generally rectangular in shape. An individual bracket was provided with a horizontal arch wire slot which was disposed centerally of the tie wings and was aligned with the other horizontal components of the assembly.

This type of apparatus and associated procedure were effective in moving teeth, but it necessitated the bending of the arch wire between adjacent brackets in order to provide the arch wire with a perpendicular orientation with respect to the tooth long axis. It was impossible to exactly duplicate these bends in the replacement of succeeding arch wires so that it was difficult to maintain a continuity of tooth movement.

In order to accommodate an unbent arch wire, sometimes referred to as a passive arch wire, Andrew's disclosed in U.S. Pat. No. 3,477,128 that the slot in the brackets could be cut at an angle. These brackets were otherwise rectangular and had the same horizontal and vertical components. Only the slot remained substantially parallel to the occlusal plane of the teeth. In a banding procedure, orientation of the tie wings is highly dependent upon the positioning of the associated band. However, once the band is mounted, the orientation of the tie wings is generally accepted. In U.S. Pat. No. 3,353,271, Blechman disclosed another banding system having a passive arch wire.

More recently, the banding procedure has given way to a procedure for bonding a bracket assembly directly to the facial surface of the tooth. With such an apparatus, the tie wings are fixed to a bonding pad which is then adhered to the tooth. Alignment of the bracket is just as critical as it was in the banding procedure; however, the bonding pads have been far more difficult to orient with the occlusal plane and the long axis of the tooth. One reason for this is that the generally rectangular brackets used in the banding procedure have also been used in the bonding procedure. Even with the angled slot, these brackets have failed to provide substantial components that could be aligned with the occlusal plane. Furthermore, the angled slot has produced a point of weakness at the gingival tip of the distal tie wing and at the occlusal tip of the mesial tie wing. In addition, the opposite tips of these tie wings have extended far beyond the arch wire plane so that the gingival tip of the mesial tie wing has tended to interfere with the gingiva and the occlusal tip of the distal tie wing has tended to interfere with mastication. Even with the angularly slotted brackets, it has been difficult to visualize the position of a passive arch wire with these bonding bracket assemblies.

SUMMARY OF THE INVENTION

In accordance with the present invention, an orthodontic bracket assembly is provided with a rhomboidal configuration which has a significant number and length of edges for alignment both with respect to the crown long axis and the occlusal plane. The tips of the tie wings can be of the same size and shape so that there are no weakened areas of the bracket. Furthermore, the tie wing tips can extend an equal distance from the arch wire so there is no protruding tie wing to interfere with the gingiva or with the opposite incisal edge during mastication.

In accordance with this invention, the bonding pad is provided with side edges which align with the tooth long axis. Similarly, the tie wings are provided with generally vertical edges which are also adapted for alignment with the tooth long axis. It is of particular importance that the tie wings also include generally horizontal components which, together with the edges of a bracket flange are disposed relative to the generally vertical edges provided at the particular angle referred to above. Thus, the edges of the tie wings in a front elevational view have a generally rhomboidal configuration.

When mounted on the tooth, the vertical components of the assembly, including the edges of the tie wings and the sides of the bonding pad, can be aligned with the tooth long axis. The horizontal components of the assembly—including the gingival and occlusal edges of the tie wings, the edges of the bracket flange, and the edges of the slot—can be aligned with the occlusal plane. Thus, the prominent edges on the tie wings provide components which can be aligned with the occlusal plane as well as the tooth long axis. Furthermore, alignment with one reference provides a check on the alignment with the other reference. Not only does this facilitate alignment of the brackets, but it makes is considerably easier to visualize the position of the passive arch wire.

These and other features and advantages of the invention will be more apparent with a discussion of preferred embodiments and reference to the associated drawings.

DESCRIPTION OF THE DRAWINGS

FIG. 1 is a front elevational view of the lower skeletal structure of the head illustrating the maxillary and the mandibular teeth and the occlusal plane defined therebetween;

FIG. 2 is a side elevational view illustrating the left side of the tooth structure and bracket assemblies of the present invention mounted thereon;

FIG. 3 is a front elevational view of one embodiment of the bracket assembly of the present invention;

FIG. 4 is a cross-sectional view of the bracket assembly taken along lines 4—4 of FIG. 3;

FIG. 5 is a cross-sectional view of the bracket assembly taken along lines 5—5 of FIG. 3;

FIG. 6 is a front elevational view of a cuspid having an appliance of prior art mounted thereon;

FIG. 7 is a front elevational view of a cuspid having another appliance of prior art mounted thereon;

FIG. 8 is a front elevational view of a cuspid having one embodiment of the bracket assembly of the present invention mounted thereon; and FIG. 9 is a front elevational view of the central and lateral incisors of the maxillary teeth having bracket assemblies of the present invention mounted thereon.

DESCRIPTION OF PREFERRED EMBODIMENTS

One form of an orthodontic appliance of the present invention is illustrated in greatest detail in FIG. 3. This appliance includes a bonding pad 11, a flange 13, and a pair of tie wings 15 and 17. This appliance is commonly referred to as a bracket assembly 19 and is particularly adapted for use in straightening teeth such as those designated generally by the reference numeral 21 in FIG. 1. The teeth 21 include upper teeth which are fixed to the upper jaw or maxilla 22. These teeth are commonly termed maxillary teeth 23. Similarly, the lower teeth are fixed to the lower jaw or mandible 24. These lower teeth are commonly termed mandibular teeth 25. Each of the maxillary and mandibular teeth, 23 and 25 respectively, include a pair of central incisors, lateral incisors, cuspids, first bicuspids, second bicuspids, first molars, second molars and third molars. These pairs of teeth are designated consecutively by the odd reference numerals 27 through 41.

Of particular interest to the present invention is the occlusal which is defined by the surface of the bicuspids and molars, 33-41, where they meet the opposing tooth in the closure of the jaws 22 and 24. In combination, these surfaces generally defined an occlusal plane 45 which also includes the incisal edges of the anterior teeth, such as the incisors and cuspids 27-31. In FIG. 1, this occlusal plane is illustrated as a line and designated generally by the reference numeral 47. It will be appreciated that although the occlusal in combination is referred to as a plane, it is not exactly planar particularly when the teeth 21 are irregular.

Locations in the mouth are commonly referred to with reference to the occlusal plane 47 and the gum tissue or gingiva 49. Directions are referred to generally as mesial (or toward a midline 51), and distal (or away from the midline 51).

FIG. 2 illustrates the teeth 23 and 25 in a side elevational view with an individual bracket assembly 19 mounted on two of the maxillary teeth 27 and 31. These bracket assemblies 19 are connected by an arch wire 55 which is preferably disposed in a substantially parallel relationship with the occlusal plane 47. The arch wire can be terminated in a buccal tube/bracket as illustrated on the first molar 37.

A ligature wire 53 is commonly provided to retain the arch wire 55 and the bracket assembly 19 in a fixed relationship. For purposes of clarity, the ligature wire 53 is illustrated only in combination with bracket 19 on the central incisor 27.

As best illustrated in FIGS. 2 and 9, each of the teeth 21 in a facial view, that is a buccal or libial view, will normally be disposed at an angle with respect to the occlusal plane 47. For example, with reference to the second bicuspid 35 in FIG. 2, the tooth is seen to include a crown 57 and a root 59 having an apex 61. With respect to this structure, each of the teeth 21 is said to have a tooth long axis which extends from the apex 61 of the root 59 to the tip of the crown 57. In FIG. 2 this tooth long axis is designated by the referenced numeral 63.

The tip of the crown 57 is well defined in the cuspids 31-35 and the molars 37-41. However, the incisors 27 and 29 have no cusps so the long axis is typically defined with reference to the midpoint of the incisal edge. Similarly, in teeth such as the molers 37-41, there will typically be more than one root 59 so that the apex 61 is defined generally with reference to the entire root structure. Without regard to these dissimilarities of the teeth, it is generally well excepted that each of the teeth 21 has a tooth long axis 63 and each long axis has a preferred or normal acute angle with respect to the occlusal plane 47. In FIGS. 2 and 9, this normal angle is referred to with the reference letter A.

One form of the bracket assembly 19 of the present invention is illustrated in FIGS. 3, 4 and 5. In this embodiment, the bonding pad 11 may include a base 71 and a mesh 73 as disclosed and claimed by Miller in U.S. Pat. No. 4,068,379. The flange 13 is commonly fixed to the base 71 on the side thereof opposite the mesh 73. In some embodiments, the flange 13 provides means for welding the tie wings 15, 17 to the bonding pad 11. However, in a preferred embodiment the flange 13 is integral with the tie wings 15 and 17 and is brazed to the base 71. In another embodiment, extensions of the flange 13 beyond the tie wings 15 and 17 may be entirely eliminated as illustrated in FIG. 8. The flange 13 also provides means for spacing the tie wings 15, 17 from the bonding pad 11.

The bonding pad 11 will typically have a generally rectangular configuration which is symmetrical about an X axis and a Y axis. The bonding pad 11 will typically be curved around each of the X axis and the Y axis to fit the facial surface of the associated tooth 21. It will be appreciated that the advantages associated with the instant invention can be achieved with any base means such as the bonding pad 11 or a band which is also commonly used in orthodontics.

With further reference to FIG. 3, it will be assumed that the bracket 19 illustrated is to be associated with one of the maxillary teeth 23 on the left side of the arch. With this association, the bonding pad 11 will typically include a mesial edge 75 and a distal edge 77 which are parallel to the Y axis, and a gingival edge 79 and occlusal edge 81 which are parallel to the X axis. It will be appreciated that these edge designations will vary with the location of the teeth 21 in the different quadrants of the mouth.

With this association, the tie wing 15 is commonly referred to as a mesial tie wing and the tie wing 17 is referred to as the distal tie wing. Each of these tie wings 15 and 17 has a facial surface 85 which is defined by a mesial edge 87, a distal edge 89, a gingival edge 91, and an occlusal edge 93. For purposes of alignment, as subsequently explained in greater detail, it is desirable that the edges 87 and 89 be substantially parallel to the Y axis and the edges 91 and 93 be disposed at the angle A to the Y axis. Since the angle A is an acute angle, it can be appreciated that the tie wings 15 and 17 in the facial view will have a generally rhomboidal configuration. It should be noted that in FIG. 3, the angle A is exaggerated to emphasize the relative positions of the components of the bracket assembly 19.

Portions of the tie wings 15 and 17 define a slot 95 which is adapted to receive the arch wire 55. The slot 95 will typically be defined by surfaces which intersect the facial surface 85 at a gingival edge 97 and an occlusal edge 99. In a preferred embodiment, these edges 97 and 99 are substantially parallel to the edges 91 and 93 of the tie wings 15 and 17. In one preferred embodiment, the tie wings 15, 17 are separated by a distance approximately equal to the combined width of the tie wings 15, 17.

As with the other components in the bracket assembly 19, the flange 13 may also be defined by gingival and occlusal edges, 101 and 103 respectively, which are substantially parallel to the edges 91 and 93 of the tie wings 15 and 17. Lateral edges 102 and 104 of the flange 13 may be aligned substantially parallel to the edge 87, 89 of the tie wings 15, 17 and the edges 75, 77 of the base 71.

One of the most significant advantages of the present invention is associated with the alignment of the bracket 19 with respect to the long axis 63 of the associated tooth 21 and the occlusal plane 47. Before referring to the next drawing it will be helpful to appreciate that the ease of placing two lines in a parallel relationship is enhanced by the length of the lines and the close proximity of the lines. Both of these considerations are emphasized in the present invention wherein the bracket 19 is provided with an increased number and length of edges which are more closely positioned to the alignment references associated with the tooth.

In aligning an orthodontic bracket on a tooth as illustrated in FIGS. 6-9, it is desirable that the slot 95 be placed in a substantially parallel relationship with the occlusal plane 47. It is also desirable that the Y axis of the bracket 19 be placed along the long axis 63 of the tooth 21. In the past, brackets have been configured as illustrated in FIG. 6 with the slot cut at an angle with respect to the tie wings. This has produced substantially weakened areas of the tie wing as illustrated generally at 109 and 111. The tie wings of these brackets have a generally rectangular configuration with their mesial and distal edges aligned with the tooth long axis. Only the edges of the slots have provided any reference for alignment with the occlusal plane. More specifically, the edges of the tie wings have not provided any means for alignment with the occlusal plane. A further disadvantage of the bracket illustrated in FIG. 6 is associated with the tips of the tie wings which are opposite the weakened areas 109 and 111. It will be noted that the gingival tip 113 of the mesial tie wing tends to extend above the adjacent tip of the distal tie wing. When mounted on certain of the teeth 21, this tip 113 tends to interfere with the gingiva. For example, a typical gingiva line 114 for an erupting cuspid of a twelve year old is shown to contact the tip 113 in FIG. 6. Similarly, the occlusal tip 115 of the distal tie wing extends below the adjacent tip of the mesial tie wing. This tip 115 can interfere with mastication particularly on the anterior teeth which close in an overbite relationship.

In a further embodiment of the prior art illustrated in FIG. 7, the flange and tie wings have been rotated with respect to the bonding pad so that the slot can be cut across the center of the tie wings. This avoids the areas of weakness 109 and 111 associated with the bracket in FIG. 6. The rectangular configuration of these tie wings provides edges which can be aligned perpendicular to the occlusal plane. However, in this bracket the tie wings provide no edges which can be aligned with the long axis 63 of the tooth 21. Although the edges of the bonding pad provide some reference for alignment with the tooth long axis, these edges are less prominent than those of the tie wing and are substantially removed from the axis 63.

Referring now to FIG. 8, one form of the bracket assembly 19 of the present invention is illustrated with its Y axis aligned along the long axis 63 of the tooth 21. In this case, the more prominent tie wings are provided with edges which align with the tooth long axis 63 and are also provided with edges which align with the occlusal plane 47. Thus, the edges 91 and 93 of the tie wings, as well as the edges 97 and 99 of the slot 95 and the edges 101 and 103 of the flange 13, provide significant components for alignment with the occlusal plane 47. The combined length of these edges as well as their greater proximity to the occlusal plane substantially increase the ease with which the bracket 19 can be aligned on the tooth 21. The tie wings also provide significant edges 87, 89 which, in combination with the edges 75 and 77 of the pad 11, can be aligned with the tooth long axis 63. Thus, the tie wings 15, 17 provide edges for alignment with each of the references of interest. In practice, alignment with one of the references provides a check on the alignment with the other reference.

Not only does the rhomboidal configuration of the tie wings 15 and 17 significantly enhance alignment of the bracket 19, but it also enables the slot 95 to be cut centerally of the tie wings 15 and 17 to avoid creating any areas of weakness. In addition, there are no tie wing tips which extend beyond the adjacent tie wing tips to interfer with either the gingiva or mastication by the teeth.

FIG. 9 illustrates a pair of maxillary central incisors 27a, 27b and a pair of maxillary lateral incisors 29a and 29b. One of the brackets 19 associated with present invention is mounted on each of these teeth. In this Figure, it is particularly apparent that only the crowns 57 of the teeth 21 will be visible when the brackets 19 are mounted. Since the apex 61 of the root 59 is hidden in the gingiva, it is not possible to accurately define the tooth long axis 63. Thus, the bracket 19 will typically be aligned with respect to a long axis 115 associated with the crown 57. The crown long axis 115 is considered a fair approximation of the tooth long axis 63.

FIG. 9 also illustrates that not only does the configuration of the bracket 19 facilitate alignment with an individual tooth, but in combination, the tie wings 15, 17 of the brackets 19 produce a locus of points (illustrated by lines 117) which can also be referenced to the occlusal plane 47. In addition, the edges 97 and 99 of the slots 95 more visibly define the passive condition of the arch wire 55.

The preferred angle A associated with the various components of the bracket 19 will vary for each of the teech 21. These preferred angles A are set forth in Table I for each of the teeth 21.

TABLE I

| Tooth | ANGLE A Maxillary | Mandibular |
|---|---|---|
| Central Incisors | 5° | 2° |
| Lateral Incisors | 8° | 2° |
| Cuspid Incisors | 10° | 6° |
| First Bicuspids | 2° | 2° |
| Second Bicuspids | 2° | 2° |
| First Molars | 5° | 2° |

It will be appreciated that although the invention has been described with reference to particular embodiments, other embodiments will now be apparent. For example, it will be apparent that the base of the bracket may take the form of a band as well as a bonding pad. Similarly, a particular bracket may include only a single tie wing. For this reason, the scope of the invention should be ascertained only with reference to the following claims.

We claim:

1. An orthodontic bracket assembly for use with an archwire to impart corrective forces on a tooth, including:
a base pad for attachment to the tooth,
a distal tie wing fixed to said base pad and including a gingival tip and an occlusal tip defining between them an archwire slot,
a mesial tie wing fixed to said base pad and including a gingival tip and an occlusal tip defining between them an archwire slot, each of said distal and mesial tie wings having parallel distal and mesial sides,
said archwire slots being in mutual alignment and providing a reference line for orientation parallel to the occlusal plane of a patient,
said sides of said tie wings are inclined at an oblique angle to said reference line, whereby said tie wings can be generally vertically disposed parallel to the tooth long axis and still be inclined at an oblique angle to said reference line,
said gingival tips and said occlusal tips of said tie wings having respectively top and bottom surfaces which are in mutual alignment parallel to said reference line and substantially equidistant therefrom,
whereby said tie wings together form a rhomboidal configuration and the axis of said archwire slots bisects said tie wings so that said gingival tips and said occlusal tips are of equal size.

* * * * *